United States Patent [19]

Silvermint

[11] Patent Number: 5,012,316
[45] Date of Patent: Apr. 30, 1991

[54] MULTIAXIAL TRANSDUCER INTERCONNECTION APPARATUS

[75] Inventor: Emanuel H. Silvermint, Shoreview, Minn.

[73] Assignee: Cardiac Pacemakers, Inc., St. Paul, Minn.

[21] Appl. No.: 329,533

[22] Filed: Mar. 28, 1989

[51] Int. Cl.$^5$ .......................................... H01L 29/84
[52] U.S. Cl. .......................................... 357/26; 73/727
[58] Field of Search .................................. 357/74, 26

[56] References Cited

U.S. PATENT DOCUMENTS

| | | | |
|---|---|---|---|
| 3,916,365 | 10/1975 | Giachino | 357/26 |
| 3,918,019 | 11/1975 | Nunn | 357/23.1 |
| 4,314,562 | 2/1982 | Ware | 128/419 P |
| 4,379,998 | 4/1983 | Shockley et al. | 357/26 |
| 4,498,229 | 2/1985 | Wilner | 357/26 |
| 4,672,411 | 6/1987 | Shimizu et al. | 357/26 |
| 4,843,454 | 6/1989 | Kato et al. | 357/74 |

FOREIGN PATENT DOCUMENTS

| | | | |
|---|---|---|---|
| 0292014 | 11/1988 | European Pat. Off. | 357/26 |
| 0154075 | 9/1984 | Japan . | |
| 0174978 | 7/1987 | Japan | 357/26 |

OTHER PUBLICATIONS

Endevco Products catalog featuring Model 2258-10-/-100 Istotron Integral Electronics Triaxial Accelerometer.
Bruel & Kjaer excerpt from 1988 Short Form Catalog including Type 4321 Triaxial Accelerometer.

Primary Examiner—Andrew J. James
Assistant Examiner—Viet Q. Nguyen
Attorney, Agent, or Firm—Haugen and Nikolai

[57] ABSTRACT

A multiaxial transducer interconnection apparatus. The apparatus comprises first, second and third substrate modules each having a plurality of electrical tracks thereon. A portion of the electrical tracks is structured and arranged to interconnect the substrate modules in an orthogonal relationship to each other. The plurality of tracks on each substrate module is further arranged to form a pattern identical to the plurality of tracks on the other substrate modules. The substrate modules each include a mounting region whereon transducer die elements are mounted. One alternate embodiment of the invention would include a base upon which the modules would mount. Another alternate invention of the invention employs a chip carrier to support the multiaxial transducer of the invention.

10 Claims, 5 Drawing Sheets

MULTIAXIAL TRANSDUCER INTERCONNECTION APPARATUS

BACKGROUND OF THE INVENTION

I. Field of the Invention

The invention is directed generally to a multiaxial interconnection apparatus for transducers and, more particularly, to a multiaxial transducer interconnection apparatus for use in advanced rate adaptive cardiac pacemaker systems, defibrillators, cardioverters, heart monitors, metabolic need indicators and similar medical electronic devices.

II. Discussion of the Prior Art

Heart and respiration activity generates mechanical energy. This energy propagates through the body and can be detected by appropriate transducers and may provide information useful for the control of organ functions such as heart rate pacing, for example. Current transducer technology does not address certain critical aspects of such medical electronics applications.

Some prior approaches in the medical electronics art use active (piezoelectric) transducer elements which are well known such as Bruel & Kjaer Company's Type 4321 and Endevco Company's Model 2258-10/-100 devices. These devices are limited in their application, however, because they do not utilize the cost and size advantages of micromachining technology.

Passive transducers are also known in the prior art. Passive transducers require excitation energy to operate. In the case of a multiaxial transducer, the number of supply lines is proportional to the number of uniaxial transducer components assembled together. The reduction in quantity of transducer terminals or wires is critical for many applications. A number of companies offer passive (piezoresistive) transducers such as IC Sensors, 1701 McCarthy Boulevard, Mulpitas, Cal., for example. These devices are sensitive in one dimension only, but could be integrated into a multiaxial transducer. However, it is believed that the die substrates currently utilized in the industry, have no designed-in features to aid in substrate-to-substrate electrical connection.

This invention provides a multiaxial transducer, useful for medical electronics applications, comprising transducer elements mounted on electrically interconnected modular substrates. The multiaxial transducer of the invention achieves a reduction in the quantity of terminals required for many applications as compared to other known devices. A multiaxial transducer interconnection apparatus is disclosed. The apparatus comprises first, second and third substrate modules each having a plurality of electrical tracks thereon. A portion of the electrical tracks is structured and arranged to interconnect the substrate modules in an orthogonal relationship to each other. The plurality of tracks on each substrate module is further arranged to form a pattern identical to the plurality of tracks on the other substrate modules. The substrate modules each include a mounting region whereon transducer die elements are mounted. The apparatus disclosed in the invention may be used in an improved advanced rate adaptive heart pacemaker system including a multiaxial transducer as disclosed by the invention as a sensing component of such a system.

One alternate embodiment of the invention includes a base upon which the modules would mount. Another alternate embodiment of the invention employs a chip carrier to support the multiaxial transducer of the invention.

OBJECTS OF THE INVENTION

It is one object of the invention to provide a multiaxial transducer comprising transducer elements mounted on substantially identically fabricated substrates.

It is another object of the invention to provide a substrate assembly for a multiaxial transducer including a plurality of transducer dies having die bonding pads wherein the ratio of substrate bonding pads per die bonding terminals is equal to or greater than three and wherein the location of the substrate bonding pads allows for pad-to-pad electrical connections of substrate modules.

It is yet another object of the invention to provide a multiaxial transducer for use as a sensing element on an advanced rate adaptive cardiac pacer system.

It is yet another object of the invention to provide a multiaxial transducer assembly fabricated from identical substrate elements so as to allow use of identical masks for the basic substrate module fabrication.

Other features, objects and advantages of the invention will become apparent to those skilled in the art through the description of the preferred embodiment, claims and drawings herein.

BRIEF DESCRIPTION OF THE DRAWINGS

In the drawings like numerals refer to like elements.

DESCRIPTION OF THE PREFERRED EMBODIMENT

Figure 1:
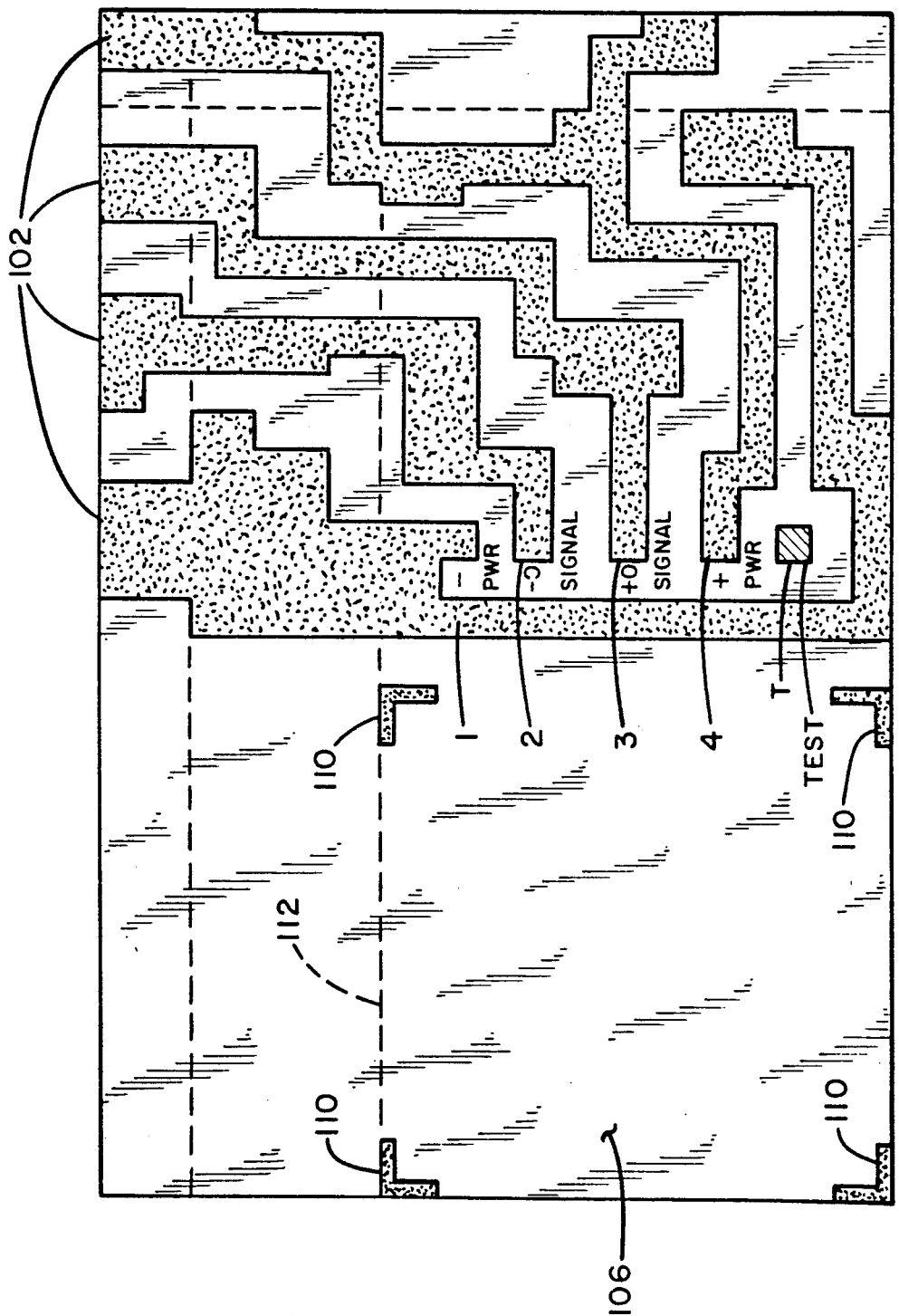
FIG. 1 shows a plan view of one embodiment of a die substrate module as provided by the invention.
Figure 3:
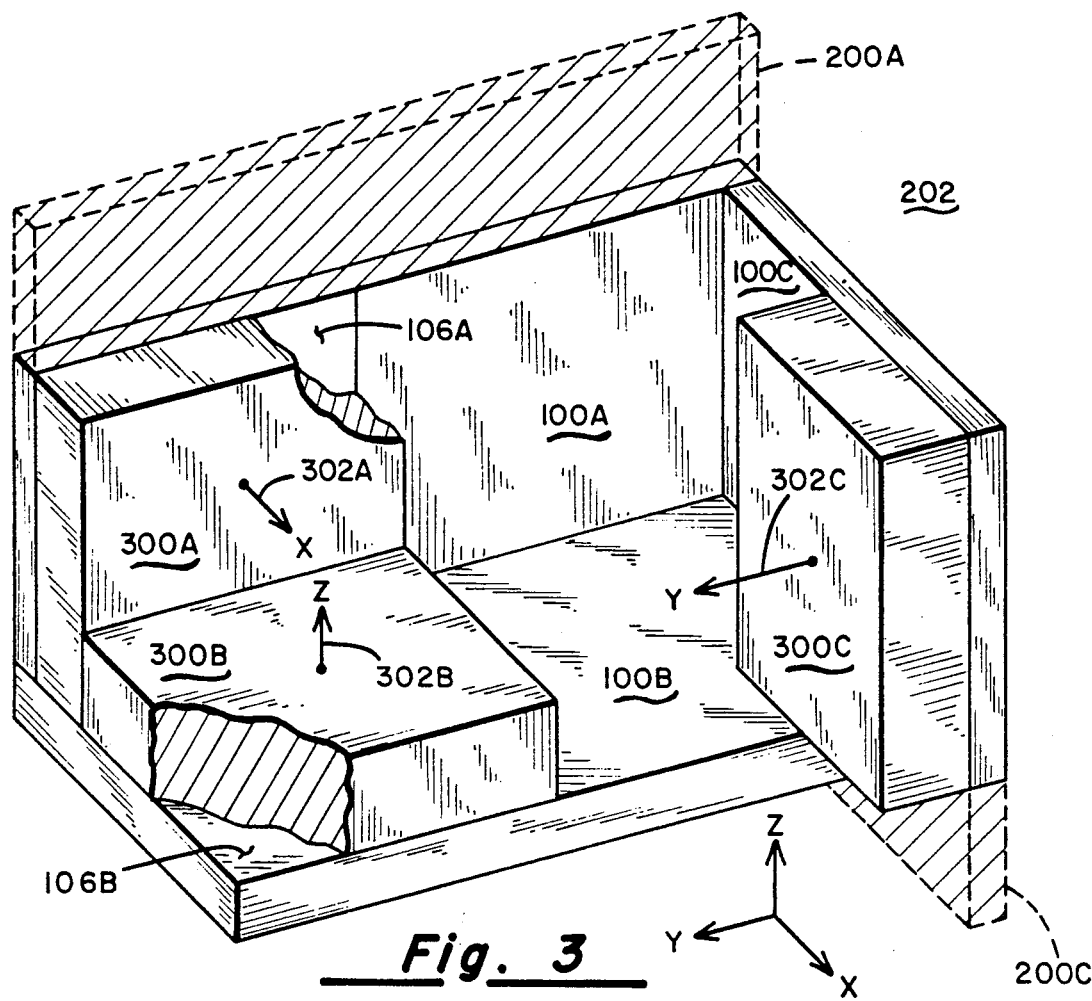
FIG. 3 shows a perspective view of one embodiment of the multiaxial transducer of the invention.

Referring now to FIG. 1, a plan view of one embodiment of a die substrate module as provided by the invention is shown. The die substrate module 100 comprises a substrate material upon which printed circuit tracks 102 for carrying electrical power or signals are deposited by means well known in the art. In one example of an embodiment of the invention, the substrate module 100 includes tracks 1, 2, 3 and 4. Track 1 is a negative voltage power line, track 4 is the positive voltage potential power line, 2 is the first signal line and 3 is a second signal line for carrying information from the transducer device to other electronics (not shown). A test pad, T, may advantageously be included. While the transducer to be used in connection with the invention is not shown in FIG. 1, the mounting surface 106 for the transducer is shown as part of the substrate module adjacent to the tracks 102 and as bordered by the corner markings 110. Broken line 112 denotes a cutting line for removing excess material from some of the modules prior to assembly as appropriate as shown in FIG. 3 and as described below in detail. The substrate module may be comprised of ceramic substrate material, for example, which may be cut by means of a laser or other cutting device well known in the art.

Figure 2:
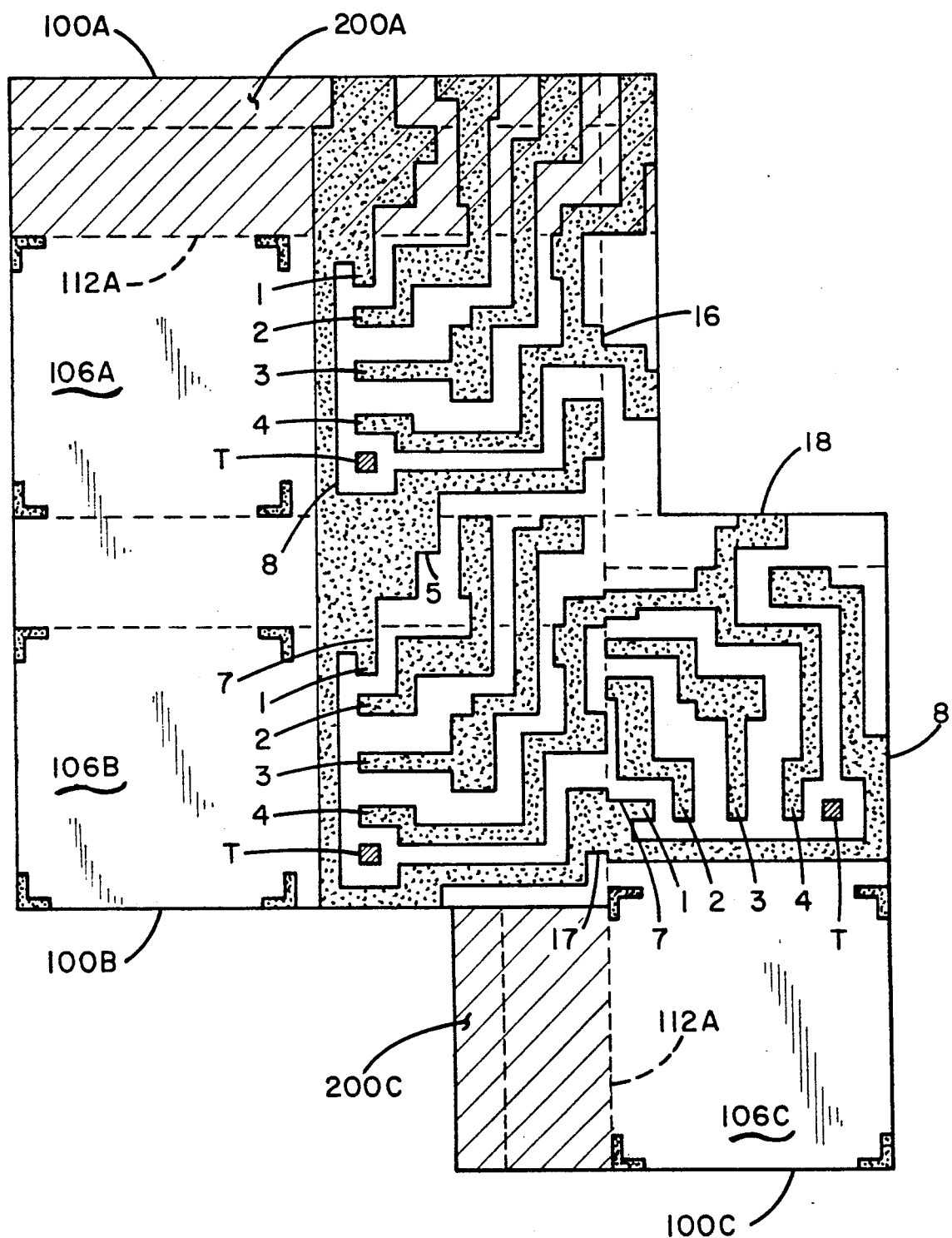
FIG. 2 shows a plan view of the interconnection scheme of one embodiment of the invention.

Referring now to FIG. 2, a plan view of an interconnection scheme of one embodiment of a substrate assembly including three die substrate modules is shown. Three substrate modules, 100A, 100B and 100C, are shown arranged for the purposes of illustrating the interconnections for this embodiment. Each of the modules 100A, 100B and 100C initially is fabricated identically as a die substrate module 100. Depending on where the module is to be used, certain modifications are made by the removal of unwanted material. Crossed-hatched areas 200A and 200C are advantageously removed prior to assembly of the three modules into a multiaxial transducer as shown in FIG. 3 by means of laser trimming or micromachine milling, for example. Note that FIG. 2 is intended to be used as an interconnection illustration only and is not representative of a manufacturing process step. Each of the substrates 100A, 100B and 100C includes a mounting surface area. These are denoted as 106A, 106B and 106C, respectively. Transducer die elements 300A, 300B and 300C as shown in FIG. 3 are advantageously affixed to the mounting surfaces prior to assembly of the modules into the multiaxial transducer. Each of the modules 100A, 100B and 100C have power and signal lines as described hereinabove with reference to module 100 in FIG. 1.

Referring now to FIG. 3, a perspective view of one embodiment of the multiaxial transducer of the invention is shown. With continuing reference to FIG. 2, it can be seen that the three substrate modules 100A, 100B and 100C have now been connected together to form a multiaxial transducer 202. Transducer devices 300A, 300B and 300C have been mounted to mounting surfaces 106A, 106B and 106C, respectively. The removed material is shown for reference purposes as 200A and 200C. No material is removed from module 100B. Modules 100A, 100B and 100C are oriented such that the mounting surfaces 106A, 106B and 106C abut each other in an orthogonal relationship. The transducer devices 300A, 300B and 300C have sensitivity axes 302A, 302B and 302C oriented in a perpendicular relationship for sensing, in this example, energy propagated in the X, Y and Z directions. Such transducer devices are well known in the art and may be, for example, accelerometers of the type as sold by IC Sensors, as for example, its 3000 Series accelerometer.

Figure 4:
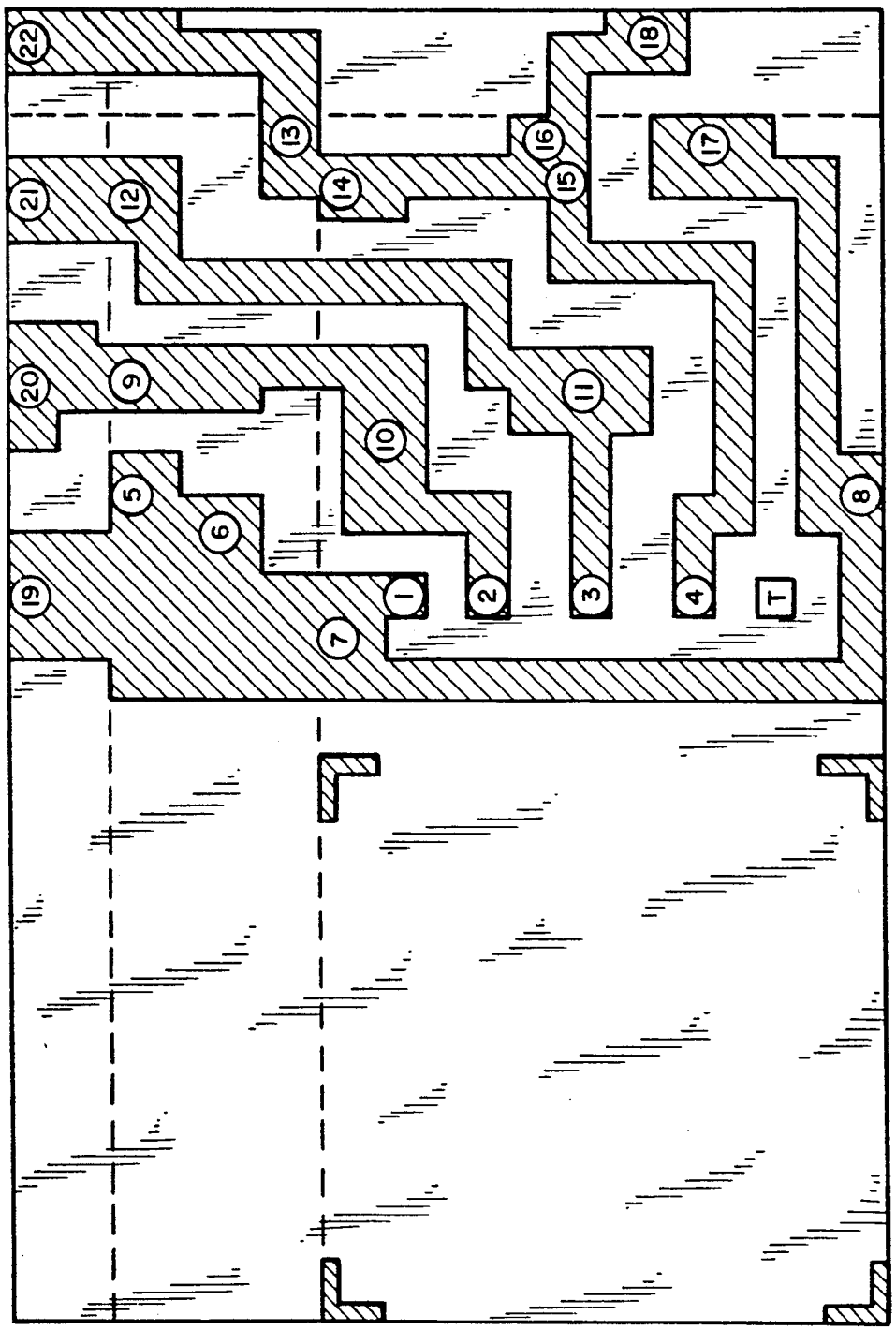
FIG. 4 is a diagram of the substrate module of the invention illustrating pad usage.

Referring now to FIG. 4, a diagram of the substrate module 100 is shown wherein each of the pad areas are designated by a reference numeral for the purposes of further clarifying the interconnections for the substrate assembly and multiaxial transducer. Those skilled in the art will recognize that this example is given by way of illustration and not limitation of the invention to the configuration shown. The table below defines the pad designations and module interconnections in accordance with the reference numerals in FIGS. 2 and 4.

| PAD | PAD DESIGNATION |
| --- | --- |
| 1 | Negative Power Supply Die Bond Pad |
| 2 | Negative Output Die Bond Pad |
| 3 | Positive Output Die Bond Pad |
| 4 | Positive Power Supply Die Bond Pad |
| 5 | Substrate Interconnection Pad 100B #5 to 100A #8 |
| 6 | Negative Power Supply Interface Wire Bond Pad |
| 7 | Substrate Interconnection Pad 100C #7 to 100B #17 |
| 8 | Substrate Interconnection Pad 100A #8 to 100B #5 |
| 9 | Alternative Pad, same as Pad #10 |
| 10 | Negative Output Interface Wire Bond Pad |
| 11 | Positive Output Interface Wire Bond Pad |
| 12 | Alternative Pad, same as Pad #11 |
| 13 | Substrate Interconnection Pad 100B #13 to 100C #14 |
| 14 | Substrate Interconnection Pad 100C #14 to 100B #13 |
| 15 | Positive Power Supply Interface Wire Bond Pad |
| 16 | Substrate Interconnection Pad 100A #16 to 100C #18 |
| 17 | Substrate Interconnection Pad 100B #17 to 100C #7 |
| 18 | Substrate Interconnection Pad 100C #18 to 100A #16 |
| 19 | Negative Power Supply Substrate Edge Connection Contact for an Alternative Uniaxial Device |
| 20 | Negative Output Substrate Edge Connector Contact for an Alternative Uniaxial Device |
| 21 | Positive Output Substrate Edge Connector Contact for an Alternative Uniaxial Device |
| 22 | Positive Power Supply Substrate Edge Connector Contact for an Alternative Uniaxial Device |
| T | Test Die Bond Pad |

The following table enumerates the pad usages and ratios for the example embodiment of the substrate module of the invention shown in FIG. 4.

| | | |
| --- | --- | --- |
| Total Pads | | 23 |
| A | Test Die Bond Pad | 1 |
| B | Alternative Pads #9 and 12 | 2 |
| C | Die Bond Pads #1-4 | 4 |
| D | Edge Connector Pads #19-22 | 4 |
| E | Interconnection Pads #5, 7, 8, 13, 14, 16-18 | 8 |
| F | Interface Wire Bond Pads #6, 10, 11, 15 | 4 |

Triaxial Transducer Pad Configuration Ratios for this example are:

$$E / C = 2$$

$$(E + F) / C = 3$$

$$(D + E + F) / C = 4$$

The above ratios would be smaller if E were equal to zero thereby providing no substrate interconnections via specially designed pads. Note that by utilizing a single substrate module 100 and a transducer 300, a unidirectional assembly can be fabricated utilizing edge connectors 19-22.

Figure 5:
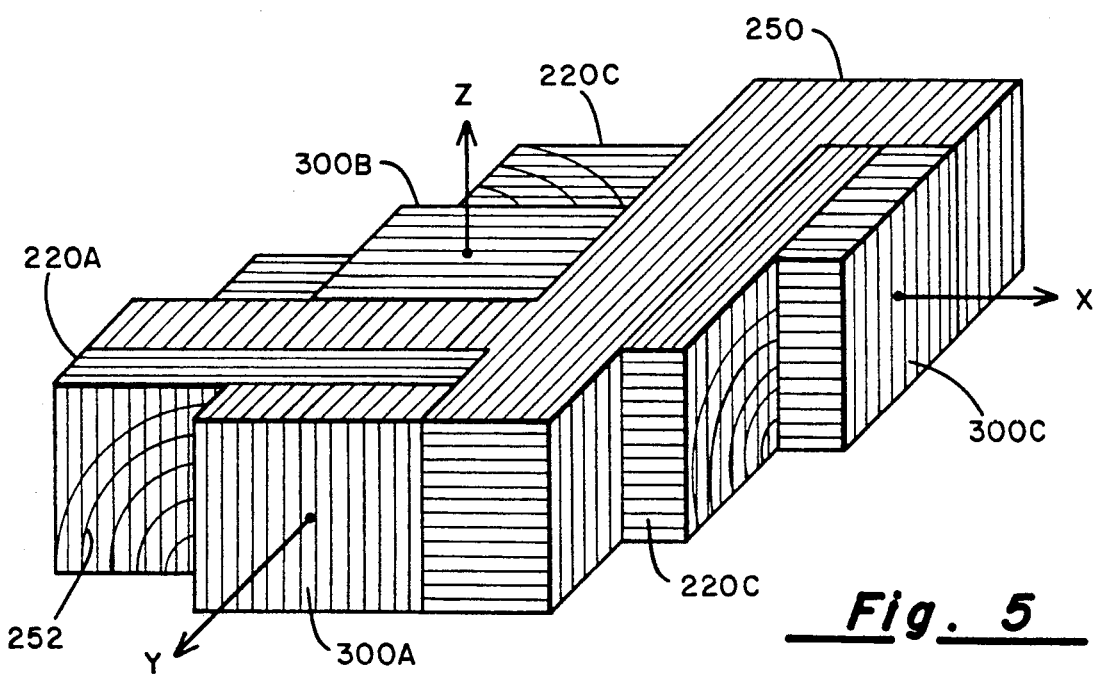
FIG. 5 shows a perspective view of an alternate embodiment of the multiaxial transducer of the invention including a base element for supporting the substrate modules.

Referring now to FIG. 5, an alternate embodiment of the multiaxial transducer of the invention is shown in perspective view. This embodiment includes transducers 300A, 300B and 300C mounted to modular substrates 220A, 220B and 220C and further mounted to base 250. Interconnections are made by means of wire conductors or tracks 252.

Figure 6:
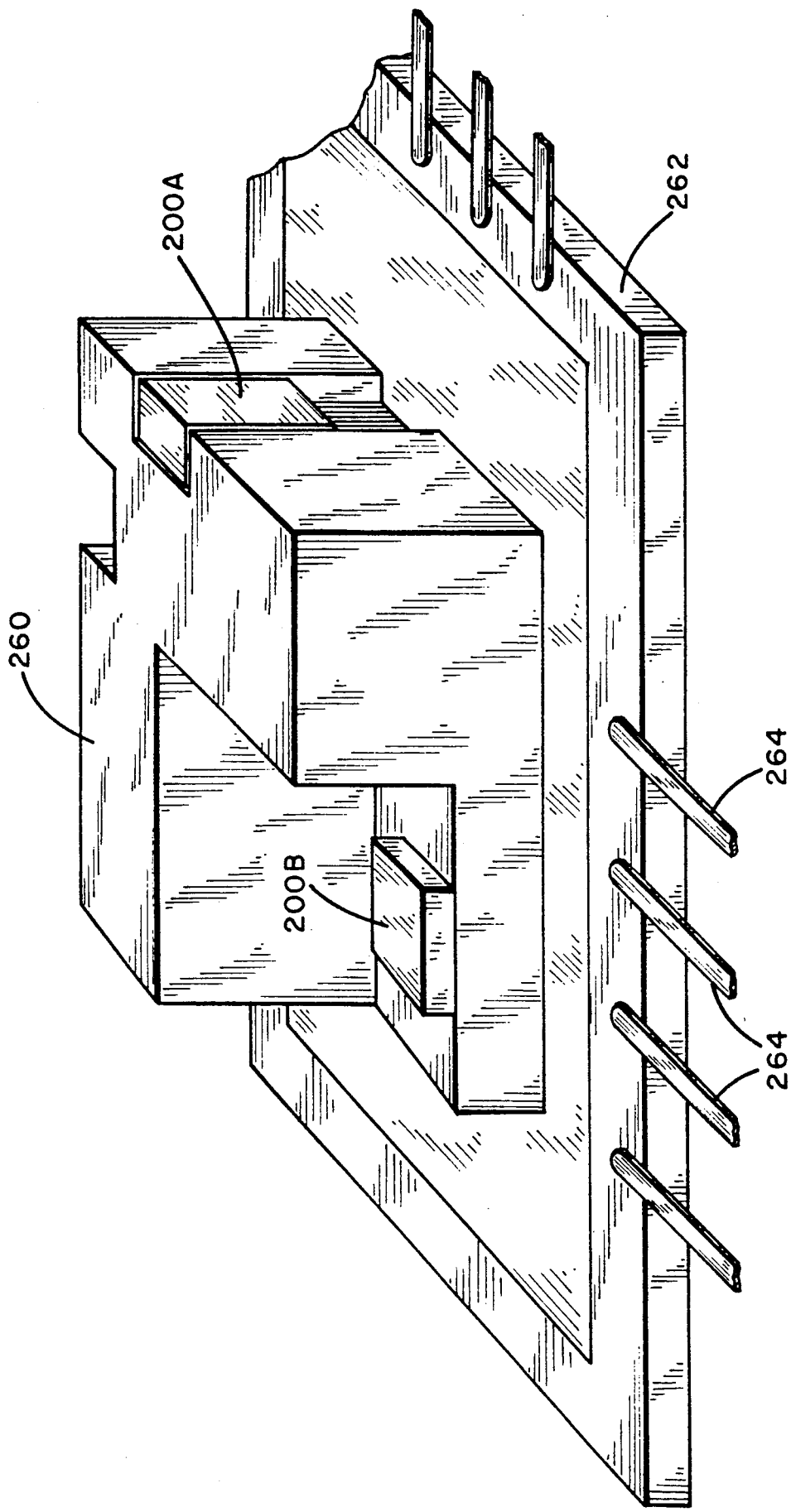
FIG. 6 shows a perspective view of another alternative embodiment of the multiaxial transducer of the invention employing a chip carrier.

Referring now to FIG. 6, yet another alternate embodiment of the invention is shown including a multiaxial transducer assembly 260 having transducers 300A, 300B and 300C (now shown) mounted on an integrated circuit chip carrier 262. Other pins 264 are then brought out from the chip carrier 262 for interfacing with external electronics. It is believed that this alternate configuration would be useful for certain applications.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. Further, those skilled in the art will recognize that the applications of the invention are not limited by the medical industry examples cited herein, but also have application to other fields utilizing multidirectional sensing devices, such as the automotive and aerospace arts.

What is claimed is:

1. A mounting apparatus for multiaxial transducer including at least two transducer die elements having bonding pads comprising:
   (a) a base having at least two orthogonal mounting surfaces; and
   (b) at least two identical substrate modules electrically interconnected to each other, each having a plurality of identical tracks, and each of which is mounted to a respective one of the mounting surfaces each including a mounting region for mounting respective one of the die elements.

2. The mounting apparatus of claim 1 which further comprises an IC chip carrier upon which the base is mounted.

3. A multiaxial transducer interconnection apparatus comprising first and second substrate modules each having a plurality of electrical tracks thereon, wherein the plurality of electrical tracks on each substrate module are structured and arranged to electrically interconnect the substrate modules in an orthogonal relationship to each other, wherein the plurality of tracks on the first substrate module is identically fabricated to form a pattern identical to the plurality of tracks on the second substrate module and wherein the substrate modules each include a mounting region.

4. A multiaxial transducer interconnection apparatus comprising first, second and third substrate modules each having a plurality of electrical tracks deposited thereon, wherein a the plurality of electrical tracks on each substrate module is structured and arranged to electrically interconnect the substrate modules in an orthogonal relationship to each other, wherein the plurality of tracks on the first, second and third substrate modules are identically fabricated when they are deposited to form identical circuit patterns to the plurality of tracks on the other substrate modules, and wherein the substrate modules each include a mounting region.

5. The apparatus of claim 4 further including first, second and third transducer die elements, each having a sensitivity axis, wherein the first, second and third transducer die elements are each mounted on respective one of the mounting regions and arranged so as to orient each sensitivity axis in an orthogonal relationship to the other sensitivity axes.

6. The apparatus of claim 3 further including first and second transducer die elements, each having a sensitivity axis, wherein the first and second transducer die elements are each mounted on respective one of the mounting regions and arranged so as to orient each sensitivity axis in a orthogonal relationship to the other sensitivity axis.

7. The apparatus of claim 1 wherein the first, second and third transducer die elements are accelerometers.

8. The apparatus of claim 6 wherein the first and second die elements are accelerometers.

9. The apparatus of claim 3 wherein the substrate modules are fabricated from ceramic material.

10. The apparatus of claim 3 wherein the plurality of electrical tracks of each module further comprise at least two tracks for carrying electrical power and at least to tracks for carrying an electrical signal.

* * * * *

UNITED STATES PATENT AND TRADEMARK OFFICE
CERTIFICATE OF CORRECTION

PATENT NO.  : 5,012,316
DATED       : April 30, 1991
INVENTOR(S) : Emanuel H. Silvermint It is certified that error appears in the above-identified patent and that said Letters Patent is hereby corrected as shown below:

Claim 4, Column 6, Line 4, delete the word "a".

Claim 4, Column 6, Lines 10-11, delete the phrase "to the plurality of tracks on the other substrate modules".

Signed and Sealed this

Twenty-second Day of September, 1992

Attest:

DOUGLAS B. COMER

*Attesting Officer*  *Acting Commissioner of Patents and Trademarks*